(12) United States Patent
Ogura

(10) Patent No.: US 8,571,254 B2
(45) Date of Patent: Oct. 29, 2013

(54) AUTHENTICATION SYSTEM AND PORTABLE MEDIUM FOR AUTHENTICATION

(75) Inventor: Masatoshi Ogura, Tokyo (JP)

(73) Assignee: JCB Co., Ltd., Tokyo (JP)

( * ) Notice: Subject to any disclaimer, the term of this patent is extended or adjusted under 35 U.S.C. 154(b) by 824 days.

(21) Appl. No.: 12/738,289

(22) PCT Filed: Nov. 16, 2007

(86) PCT No.: PCT/JP2007/072291
§ 371 (c)(1),
(2), (4) Date: Apr. 15, 2010

(87) PCT Pub. No.: WO2009/050830
PCT Pub. Date: Apr. 23, 2009

(65) Prior Publication Data
US 2010/0232715 A1 Sep. 16, 2010

(30) Foreign Application Priority Data
Oct. 19, 2007 (JP) ................................ 2007-272613

(51) Int. Cl.
*G06K 9/00* (2006.01)

(52) U.S. Cl.
USPC ..................... 382/100; 250/339.07

(58) Field of Classification Search
USPC ............... 382/100, 217; 250/339.07
See application file for complete search history.

(56) References Cited

U.S. PATENT DOCUMENTS

| 5,986,550 A | 11/1999 | Rapaport et al. |
| 7,188,768 B1 | 3/2007 | Rozumek et al. |
| 7,378,658 B2 * | 5/2008 | Mueller et al. ............ 250/358.1 |
| 7,579,596 B2 * | 8/2009 | James et al. ............... 250/341.1 |
| 7,633,299 B2 * | 12/2009 | Itsuji ............................... 324/639 |
| 7,697,745 B2 * | 4/2010 | Otani et al. .................... 382/132 |
| 7,745,792 B2 * | 6/2010 | Breit et al. ................... 250/341.8 |
| 7,782,067 B2 * | 8/2010 | Ouchi et al. .................. 324/637 |
| 7,823,338 B2 * | 11/2010 | Slagel et al. ................... 52/79.1 |
| 7,888,646 B2 * | 2/2011 | Breit et al. ................... 250/341.1 |
| 8,129,684 B2 * | 3/2012 | Mueller ....................... 250/341.8 |
| 2002/0008148 A1 | 1/2002 | Empedocles et al. |
| 2005/0083720 A1 | 4/2005 | Fukui et al. |

FOREIGN PATENT DOCUMENTS

| JP | 4076817 A | 3/1992 |
| JP | 10-509815 | 9/1998 |
| JP | 2000-306058 A | 11/2000 |
| JP | 2003-515622 A | 5/2003 |

(Continued)

OTHER PUBLICATIONS

International Search Report, PCT/JP2007/072291, dated Feb. 19, 2008.

(Continued)

*Primary Examiner* — John Strege
(74) *Attorney, Agent, or Firm* — Nixon Peabody LLP

(57) ABSTRACT

An authentication system includes: a measuring portion that radiates terahertz waves to a portable medium for authentication including materials having a characteristic oscillation frequency in a terahertz frequency band, measures a spectrum, and outputs a measurement spectrum that is a measurement result; a characteristic spectrum database which stores a characteristic spectrum of the materials; a discriminating portion that discriminates the materials that are included in the portable medium for authentication based on the measurement spectrum and the characteristic spectrum, and outputs a discrimination result.

4 Claims, 7 Drawing Sheets

(56) References Cited

FOREIGN PATENT DOCUMENTS

| | | |
|---|---|---|
| JP | 2003-531734 A | 10/2003 |
| JP | 2004-286716 | 10/2004 |
| JP | 2005-114413 | 4/2005 |
| JP | 2005-264342 A | 9/2005 |
| JP | 2006-528809 A | 12/2006 |
| JP | 2007-004572 A | 11/2007 |
| WO | 03-030097 A1 | 4/2003 |
| WO | 03058549 A1 | 7/2003 |
| WO | 2005/010801 A2 | 2/2005 |
| WO | 2007/039288 A1 | 4/2007 |

OTHER PUBLICATIONS

Japanese Office Action in Japanese Application No. 2007-272613, mailed Jul. 31, 2012.

* cited by examiner

| COMBINATION OF MATERIALS |
|---|
| A, B, C, D, E |
| A, C, D, F, G |
| B, C, F, G, H |
| ⋮ |

| COMBINATION OF MATERIALS | USER ID |
|---|---|
| A, B, C, D, E | 12345 |
| A, C, D, F, G | 23456 |
| B, C, F, G, H | 34567 |
| ⋮ | ⋮ |

| PERMUTATION OF MATERIALS |
|---|
| A, B, C, D, E |
| A, B, C, E, D |
| A, C, B, D, E |
| ⋮ |

US 8,571,254 B2

AUTHENTICATION SYSTEM AND PORTABLE MEDIUM FOR AUTHENTICATION

CROSS REFERENCE TO RELATED APPLICATIONS OR PRIORITY CLAIM

This application is a national phase of International Application No. PCT/JP2007/072291, entitled "Authentication System And Portable Medium For Authentication", which was filed on Nov. 16, 2007, and which claims priority of Japanese Patent Application No. 2007-272613, filed Oct. 19, 2007, the contents of which are incorporated herein by reference.

DESCRIPTION

1. Technical Field

The present invention relates to art that utilizes electromagnetic waves of the terahertz frequency band (terahertz waves), and in particular to an authentication system and a portable medium for authentication.

2. Background Art

For example, Patent Documents 1 and 2 disclose art that utilizes terahertz waves to perform discrimination of a material that is stored in a sealed container such as an envelope or a plastic container. In the conventional art that is disclosed in Patent Document 1, a reference spectrum of a material is measured in advance, and it is determined whether a material that has the reference spectrum is included from the output waves after radiating an object to be inspected with terahertz waves. In the conventional art of Patent Document 2, an object to be inspected is scanned in two dimensions with terahertz waves and a two-dimensional distribution of the absorbancy spectrum of the object to be inspected is measured. Next, a two-dimensional distribution of the target density is calculated from the absorbancy spectrum of a target that is measured in advance and the two-dimensional distribution of the absorbancy spectrum of the object to be inspected, and the two-dimensional distribution of the target density is two-dimensionally displayed as an image. Thereby, the shape of the target is two-dimensionally displayed as an image.

DISCLOSURE OF INVENTION

Problem to be Solved by the Invention

However, the aforementioned conventional art stops at discrimination of a material using terahertz waves and two-dimensionally displaying as an image the shape of the material. For that reason, it is not possible to control other devices of some sort from that result.

The present invention was achieved in view of the above circumstances. An object of the present invention is to provide an authentication system and a portable medium for authentication that can perform discrimination of a material using terahertz waves and control other devices from that result.

Means for Solving the Problem

In order to resolve the aforementioned issues, an authentication system according to a first aspect of the present invention includes: a measuring portion that radiates terahertz waves to a portable medium for authentication including materials having a characteristic oscillation frequency in a terahertz frequency band, measures a spectrum, and outputs a measurement spectrum that is a measurement result; a characteristic spectrum database which stores a characteristic spectrum of the materials; a discriminating portion that discriminates the materials that are included in the portable medium for authentication based on the measurement spectrum and the characteristic spectrum, and outputs a discrimination result; an authentication database which stores a combination of materials that are included in a portable medium for authentication; and an authenticating portion that outputs an authentication signal in a case where a combination of materials that is determined as being included in the portable medium for authentication by the discrimination result is stored in the authentication database.

A portable medium for authentication according to a second aspect of the present invention includes materials having a characteristic oscillation frequency in a terahertz frequency band.

An authentication system according to a third aspect of the present invention includes: a measuring portion that radiates terahertz waves to a portable medium for authentication including materials having a characteristic oscillation frequency in a terahertz frequency band while scanning in a two-dimensional manner, measures a two-dimensional distribution of a spectrum, and outputs a first measurement spectrum two-dimensional distribution that is a measurement result; a characteristic spectrum database which stores a characteristic spectrum of the materials; a discriminating portion that discriminates the materials that are included in the portable medium for authentication based on the first measurement spectrum two-dimensional distribution and the characteristic spectrum and acquires a discrimination result, and judges a permutation in a two-dimensional spatial relation of the materials determined by the discrimination result and outputs a judgment result; an authentication database which stores a permutation of materials that are included in the portable medium for authentication; and an authenticating portion that outputs an authentication signal in a case where a permutation of materials that is determined as being included in the portable medium for authentication by the judgment result is stored in the authentication database.

A portable medium for authentication according to a fourth aspect of the present invention includes materials having a characteristic oscillation frequency in a terahertz frequency band having a permutation.

An authentication system according to the present invention may further include a controlled device that operates in accordance with the authentication signal.

An authentication system according to the present invention may further include: an imaging portion that radiates terahertz waves to a holder of the portable medium for authentication while scanning in a two-dimensional manner, measures a two-dimensional distribution of a spectrum and acquires a second measurement spectrum two-dimensional distribution that is a measurement result, and produces a two-dimensional image that shows a shape of a material that the holder is carrying based on the second measurement spectrum two-dimensional distribution; an image database that stores a collation image for collation with the two-dimensional image that is produced by the imaging portion; and an image collating portion that collates the two-dimensional image that is produced by the imaging portion with the collation image in the image database, and outputs a collation result, and the authenticating portion may perform authentication on the holder based on the collation result.

An authentication system according to the present invention may further include an action database that stores action information that shows what kind of operation a controlled device that operates according to a command performs; and a command sending portion that searches for application action information according to the authorization signal from the action database, and transmits a command corresponding to the application action information to the controlled device.

Effect of the Invention

According to the present invention, a material that is included in a portable medium for authentication is discriminated using terahertz waves. Authentication is performed by a combination of materials determined by that discrimination, and an authentication signal is output. Also, according to an embodiment of the present invention, a material that is included in a portable medium for authentication is discriminated using terahertz waves. Authentication is performed by the permutation of materials determined by that discrimination, and an authentication signal is output. Thereby, it becomes possible to control another device by the authentication signal.

REFERENCE SYMBOLS

Figure 1:
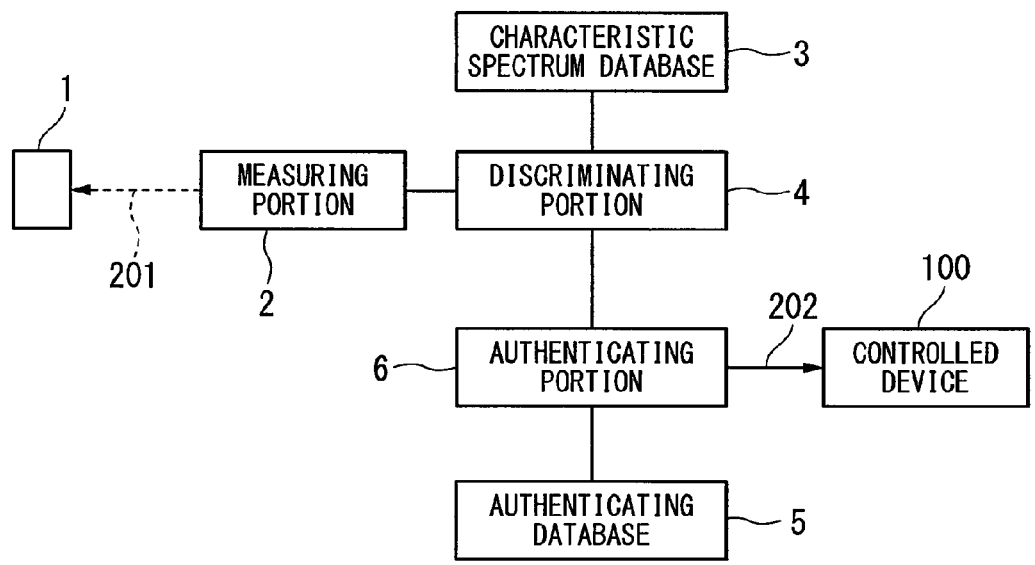
FIG. 1 is a block diagram that shows a constitution of an authentication system according to a first embodiment of the present invention.

1 Terahertz authentication card (portable medium for authentication)
2 Measuring portion
3 Characteristic spectrum database
4 Discriminating portion
5 Authentication database
6 Authenticating portion
21 Card mounting portion
22, 51 Terahertz wave generating portion
23, 53 Terahertz wave detecting portion
24, 54 Spectrum calculating portion
31, 52 Scanning portion
41 Imaging portion
42 Image collating portion
43 Image database
55 Image producing portion
61 Action database
62 Command sending device
100 Controlled device
201, 202 Terahertz wave
202 Authentication signal

BEST MODE FOR CARRYING OUT THE INVENTION (First Embodiment)

FIG. 1 is a block diagram that shows the constitution of an authentication system according to a first embodiment of the present invention. In FIG. 1, the authentication system includes a terahertz authentication card 1, a measuring portion 2, a characteristic spectrum database 3, a discriminating portion 4, an authentication database 5, and an authenticating portion 6. A controlled device 100 is a device that operates in accordance with an authentication result (authentication signal) of the present authentication system.

Figure 2:
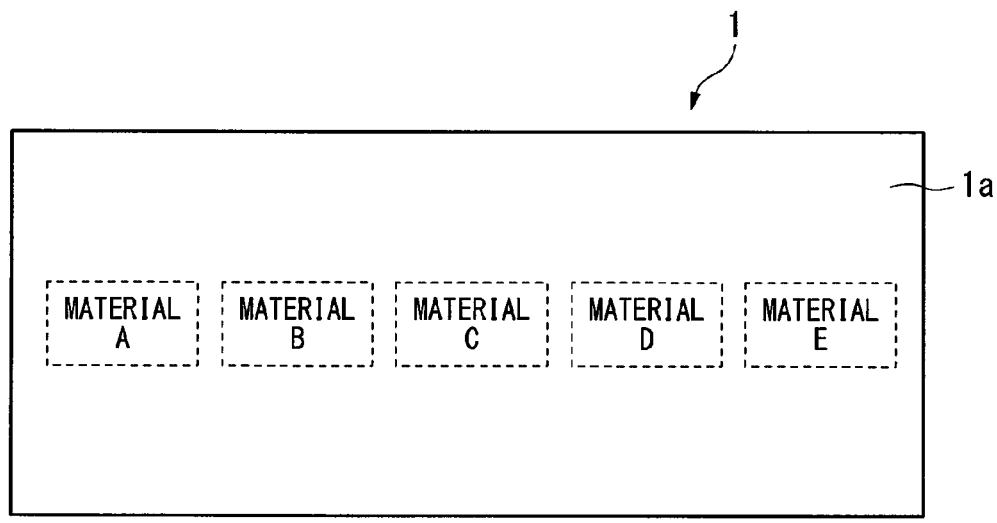
FIG. 2 is a plan view that shows a constitution of a terahertz authentication card 1 shown in FIG. 1.

FIG. 2 is a plan view that shows the constitution of the terahertz authentication card 1 shown in FIG. 1. In FIG. 2, the terahertz authentication card 1 is constituted from a card body 1a and materials that are incorporated into the card body 1a. The card body 1a is of a material quality that allows transmission of electromagnetic waves of the terahertz wavelength band (terahertz waves). Examples of materials that allow transmission of terahertz waves include paper, plastic, rubber, vinyl, wood, fiber, and ceramic. The materials that are incorporated into the card body 1a have a characteristic resonance frequency in the terahertz frequency band. In the example of FIG. 2, the five kinds of materials A, B, C, D, E are incorporated into the card body 1a. A material that has a characteristic resonance frequency in the terahertz frequency band has a characteristic spectrum (absorption spectrum) in the terahertz frequency band. An absorption spectrum which is characteristics to a material is called a fingerprint spectrum.

Figures 3, 4, 5:
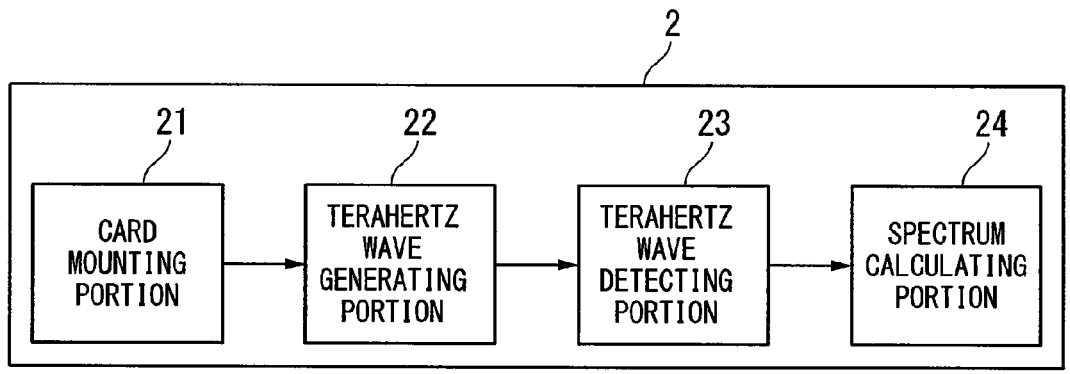
FIG. 3 is a block diagram that shows a constitution of a measuring portion 2 shown in FIG. 1.
FIG. 4 is a configuration example of an authentication database 5 shown in FIG. 1.
FIG. 5 is another configuration example of an authentication database 5 shown in FIG. 1.

FIG. 3 is a block diagram that shows the constitution of the measuring portion 2 shown in FIG. 1. In FIG. 3, the measuring portion 2 has a card mounting portion 21, a terahertz wave generating portion 22, a terahertz wave detecting portion 23, and a spectrum calculating portion 24.

The card mounting portion 21 has a mounting location for the terahertz authentication card 1, and detects the mounting of the terahertz authentication card 1 at this mounting location. The card mounting portion 21 outputs a detection signal when it detects that the terahertz authentication card 1 has been mounted at the predetermined mounting location.

The terahertz wave generating portion 22, upon receiving the detection signal from the card mounting portion 21, radiates terahertz waves 201 towards the terahertz authentication card 1 that exists at the mounting location, as shown in FIG. 1.

The terahertz wave generating portion 22 generates in order terahertz waves 201 of a plurality of frequencies defined in advance and radiates each at a predetermined period at a time. The frequency of the terahertz waves 201 is made to include at least the characteristic resonance frequency of the materials incorporated in the terahertz authentication card 1. The characteristic resonance frequency of the materials is measured in advance. The terahertz wave generating portion 22 notifies the terahertz wave detecting portion 23 that it is radiating the terahertz waves 201.

The terahertz wave detecting portion 23 detects a transmission wave of the terahertz waves 201 that are radiated from the terahertz wave generating portion 22 being transmitted through the terahertz authentication card 1. Alternatively, the terahertz wave detecting portion 23 detects a reflection wave of the terahertz waves 201 that are radiated from the terahertz wave generating portion 22 being reflected by the terahertz authentication card 1. The terahertz wave detecting portion 23 detects terahertz waves in the period while the terahertz wave generating portion 22 is radiating the terahertz waves 201, and outputs the detected signal to the spectrum calculating portion 24.

The spectrum calculating portion 24 calculates a spectrum based on the terahertz wave detection signal received from the terahertz wave detecting portion 23. The spectrum calculating portion 24 passes the calculated spectrum (hereinbelow referred to as a measurement spectrum) to the discriminating portion 4.

The description returns to FIG. 1

In FIG. 1, a characteristic spectrum is stored for each material that is incorporated in the terahertz authentication card 1 in the characteristic spectrum database 3. The characteristic spectrums of materials measured in advance, and the measurement results are turned into a database.

The discriminating portion 4, upon receiving the measurement spectrum from the measuring portion 2, discriminates and determines the materials contained in the measurement spectrum based on the characteristic spectrums in the characteristic spectrum database 3.

The discriminating portion 4 notifies the authenticating portion 6 of all the determined materials (combination of determined materials).

Combinations of materials incorporated in the terahertz authentication card 1 are stored in the authentication database 5. An example configuration of the authentication database 5 is shown in FIG. 4. In the example of FIG. 4, combinations such as "materials A, B, C, D, E", "materials A, C, D, F, G", "materials B, C, F, G, H", are stored.

Upon being informed of a combination of determined materials from the discriminating portion 4, the authenticating portion 6 searches the authentication database 5. In the case of the combination of determined materials notified from the discriminating portion 4 being stored in the authentication database 5, the authenticating portion 6 outputs an authentication signal 202 to the controlled device 100. Upon receiving the authentication signal 202, the controlled device 100 starts a predetermined operation.

Examples of the controlled device 100 include a door opening/closing device and a door locking device. Upon receiving the authentication signal 202, the door opening/closing device performs opening/closing of a door. Upon receiving the authentication signal 202, the door locking device locks or unlocks a door.

The authentication database 5, as shown in FIG. 5, may be made to store the combination of materials incorporated in the terahertz authentication card 1 as well as user identification information (user ID) for every combination. The authenticating portion 6 performs the following process in the case of a combination of determined materials notified from the discriminating portion 4 being stored in the authentication database 5. That is, the authenticating portion 6 reads the user ID that is matched with the combination of the determined materials from the authentication database 5, and outputs it to the controlled device 100 with the authentication signal 202 (the data of the user ID may be included in the authentication signal 202). Upon receiving the authentication signal 202 and the user ID, the controlled device 100 will start a predetermined operation directed to that user ID. Examples of the controlled device 100 include a credit settlement device, a security check device, and the like. Upon receiving the authentication signal 202, the credit settlement device starts the credit settlement process for that user ID. The security check device, upon receiving the authentication signal 202 and the user ID, starts the security check process for that user ID.

According to the first embodiment described above, materials that are incorporated in the terahertz authentication card 1 are discriminated using terahertz waves. Authentication is performed by the combination of those determined materials, and an authentication signal is outputted. Thereby, it is possible to control the controlled device 100 by that authentication signal.

(Second Embodiment)

In a second embodiment, authentication is performed by the permutation of materials that are incorporated in the terahertz authentication card 1. The constitution of the authentication system according to the second embodiment is the same as those of FIG. 1. Hereinbelow, the differences with the first embodiment shall mainly be explained.

Figures 6, 7:
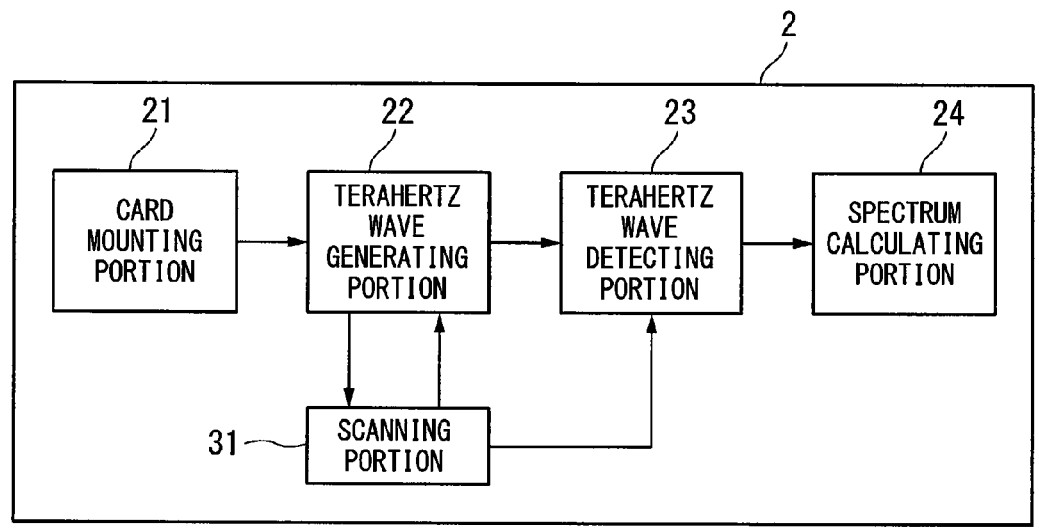
FIG. 6 is a block diagram that shows a constitution of a measuring portion 2 according to a second embodiment of the present invention.
FIG. 7 is a configuration example of an authentication database 5 according to the second embodiment of the present invention.

FIG. 6 is a block diagram that shows the constitution of the measuring portion 2 according to the second embodiment. In FIG. 6, the same reference symbols are assigned to those portions corresponding to FIG. 3. A scanning portion 31 is provided in the second embodiment.

Although the card mounting portion 21 is the same as that of the first embodiment, the terahertz authentication card 1 that is mounted in the mounting location is capable of moving within the same plane.

Similarly to the first embodiment, upon receiving a detection signal from the card mounting portion 21, the terahertz wave generating portion 22 generates and radiates in order terahertz waves 201 of a plurality of frequencies defined in advance. At this time, the terahertz wave generating portion 22 continues radiating the terahertz waves 201 of the same frequency until there is an instruction from the scanning portion 31.

Each time the frequency changes, the terahertz wave generating portion 22 notifies the scanning portion 31 that it is radiating the terahertz waves 201. Similarly to the first embodiment, the terahertz wave generating portion 22 notifies the terahertz wave detecting portion 23 that it is radiating the terahertz waves 201.

The scanning portion 31 drives the terahertz authentication card 1 that is in the card mounting portion 21 so as to cause it to move within the same plane. The scanning portion 31 moves the terahertz authentication card 1 within the same plane so that the terahertz waves 201 that are radiated from the terahertz wave generating portion 22 two-dimensionally scan a predetermined existence range of the materials that are incorporated in the terahertz authentication card 1. Thereby, it is possible to perform radiating the terahertz waves to the predetermined existence range of the materials that are incorporated in the terahertz authentication card 1 while two-dimensionally scanning.

Upon being informed that the terahertz waves from the terahertz wave generating portion 22 are being radiated, the scanning portion 31 starts movement within the same plane. When this movement within the same plane is completed, the scanning portion 31 gives an instruction to the terahertz wave generating portion 22 to radiate the terahertz waves 201 of the next frequency. The scanning portion 31 outputs a scan signal that corresponds to the movement within the same plane of the terahertz authentication card 1 to the terahertz wave detecting portion 23. The scan signal is a signal that shows the coordinates within the same plane.

The terahertz wave detecting portion 23, similarly to the first embodiment, detects the terahertz waves in the period while the terahertz wave generating portion 22 is radiating the terahertz waves 201, and outputs the detected signal to the spectrum calculating portion 24. At this time, the terahertz wave detecting portion 23 outputs, to the spectrum calculating portion 24, the terahertz wave detection signal together with the scan signal received from the scanning portion 31.

The spectrum calculating portion 24 calculates a two-dimensional distribution of the spectrum based on the scan signal and the terahertz wave detection signal received from the terahertz wave detecting portion 23. The spectrum calculating portion 24 passes the two-dimensional distribution of the spectrum that was calculated (hereinbelow referred to as a first measurement spectrum two-dimensional distribution) to the discriminating portion 4.

The discriminating portion 4, upon receiving the first measurement spectrum two-dimensional distribution from the measuring portion 2, discriminates and determines the materials contained in the first measurement spectrum two-dimensional distribution based on the characteristic spectrum in the characteristic spectrum database 3. Moreover, the discriminating portion 4 judges and determines the permutation in a two-dimensional spatial relation of the determined materials based on the characteristic spectrum of the determined materials and the first measurement spectrum two-dimensional distribution. The discriminating portion 4 notifies the permutation for all the determined materials (permutation of determined materials) to the authenticating portion 6.

As shown in FIG. 7, the permutation of the materials incorporated into the terahertz authentication card 1 is stored in the authentication database 5. In FIG. 7, for example permutation, such as "materials A, B, C, D, E", "materials A, B, C, E, D", "materials A, C, B, D, E", are stored.

The authenticating portion 6, upon being notified of the permutation of determined materials from the discriminating portion 4, searches the authentication database 5. In the case of the permutation of the determined materials notified from the discriminating portion 4 being stored in the authentication database 5, the authenticating portion 6 outputs the authentication signal 202 to the controlled device 100. The controlled device 100 starts a specified operation upon receiving the authentication signal 202.

Figure 8A:
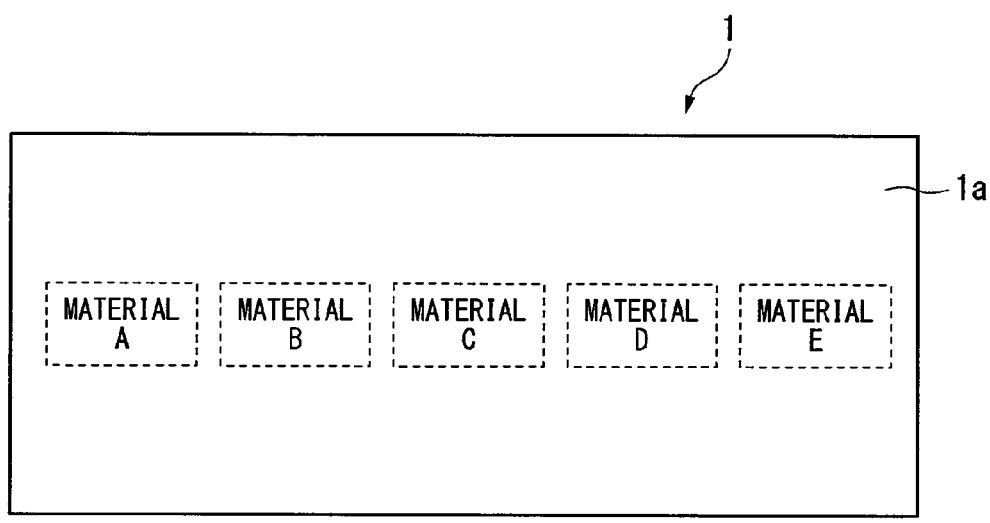
FIG. 8A is a plan view that shows a constitution of a terahertz authentication card 1 according to the second embodiment of the present invention.
Figure 8B:
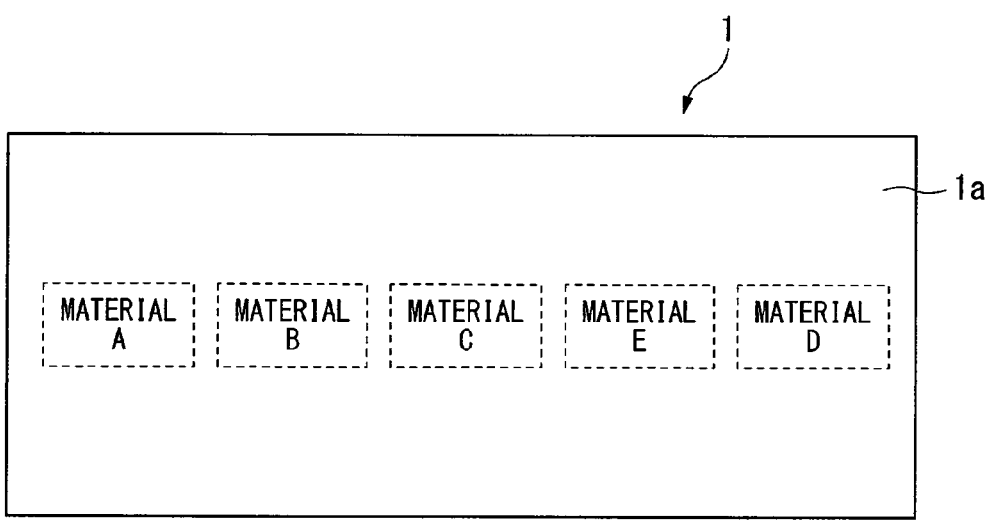
FIG. 8B is a plan view that shows another constitution of the terahertz authentication card 1 according to the second embodiment of the present invention.

FIGS. 8A and 8B are plan views showing the constitution of the terahertz authentication cards 1 according to the second embodiment. In FIG. 8A, materials A, B, C, D, and E are incorporated in the terahertz authentication card 1 in the arrangement of the permutation of "materials A, B, C, D, E." In FIG. 8B, materials A, B, C, D, and E are incorporated in the terahertz authentication card 1 in the arrangement of the permutation of "materials A, B, C, E, D." In this way, in the second embodiment, even with the materials A, B, C, D, E of the same combination, it is possible to produce different terahertz authentication cards 1 by changes in the permutation. Thereby, it is possible to expand the number of the terahertz authentication cards 1 issued.

According to the second embodiment mentioned above, materials that are incorporated in the terahertz authentication card 1 are discriminated using terahertz waves. Next, the permutation in a two-dimensional spatial relation of the materials determined by that discrimination, is judged. Next, authentication is performed by the permutation of determined materials, and an authentication signal is outputted. Thereby, it is possible to control the controlled device 100 by the authentication signal. Furthermore, even for combinations of the same materials, since it is possible to produce different terahertz authentication cards 1 by changes in the permutation, it is possible to expand the number of the terahertz authentication cards 1 issued.

It is possible to discriminate the head of the permutation by stipulating the mounting direction of the terahertz authentication card 1. The head of the permutation may also be discriminated by setting a material thereof to a specified one in advance. By doing so, it becomes unnecessary to stipulate the mounting direction of the terahertz authentication card 1.

(Third Embodiment)

In the third embodiment, imaging of materials that utilizes terahertz waves is additionally performed in the first embodiment or the second embodiment, and discriminating whether a person who holds the terahertz authentication card 1 is not for example carrying a hazardous material is done and authentication is performed.

Figure 9:
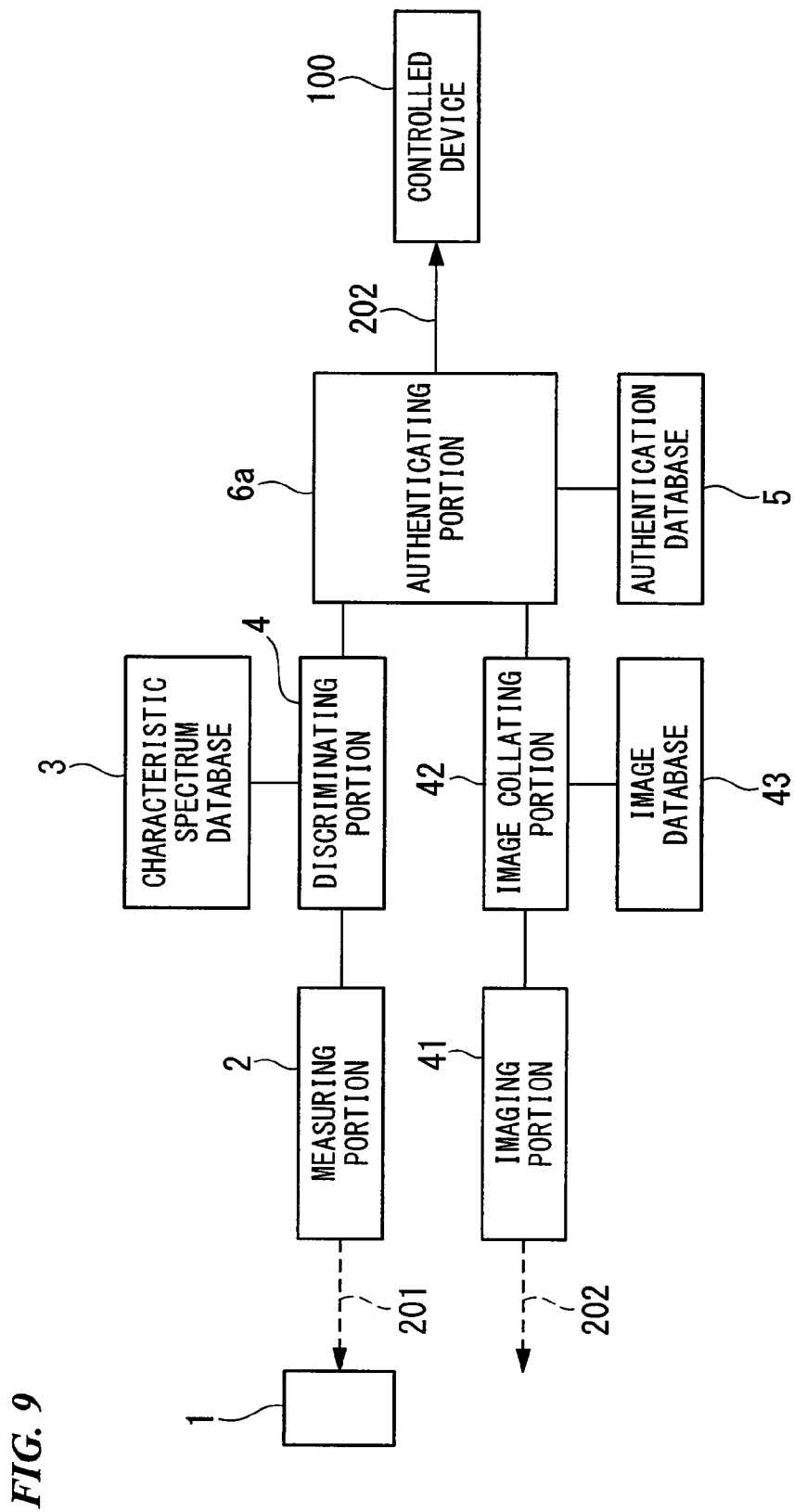
FIG. 9 is a block diagram that shows a constitution of a authentication system according to a third embodiment of the present invention.

FIG. 9 is a block diagram that shows the constitution of an authentication system according to a third embodiment of the present invention. In FIG. 9, the same reference symbols are assigned to those portions corresponding to the portions of FIG. 1. In the third embodiment, an imaging portion 41, an image collating portion 42, and an image database 43 are provided.

Figure 10:
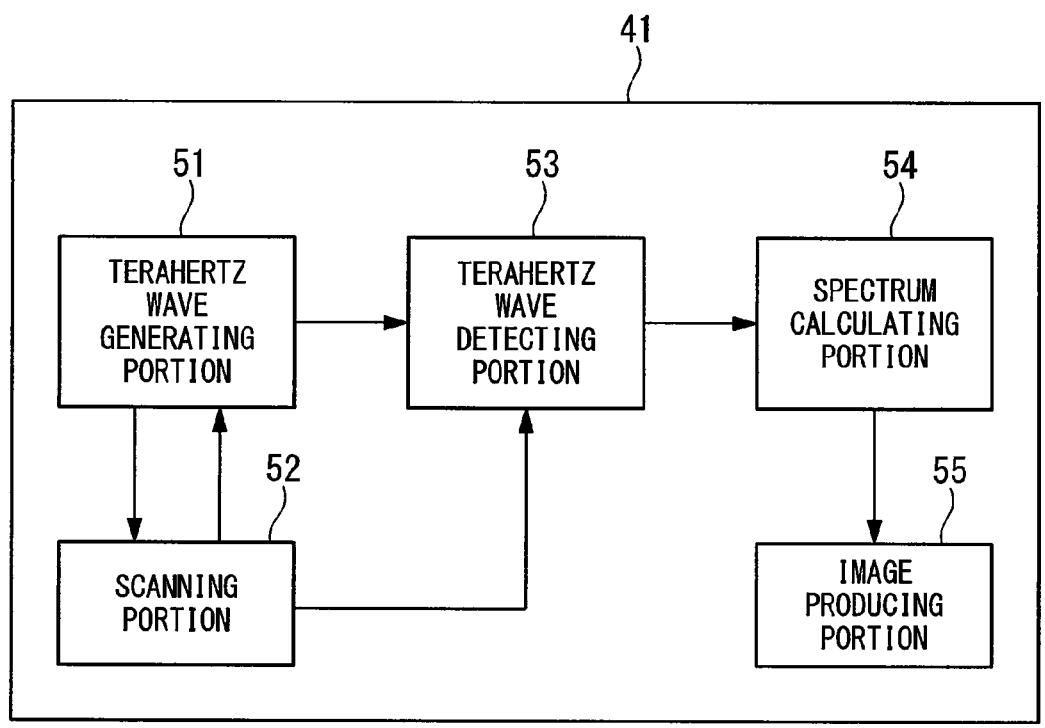
FIG. 10 is a block diagram that shows a constitution of an imaging portion 41 shown in FIG. 9.

FIG. 10 is a block diagram that shows the constitution of the imaging portion 41 shown in FIG. 9. In FIG. 10, a terahertz wave generating portion 51 radiates terahertz waves 202 towards a person holding the terahertz authentication card 1. A scanning portion 52 controls radiation operation of the terahertz wave generating portion 51 so as to radiate the terahertz waves to the holder of the card while scanning in a two-dimensional manner. The scanning portion 52 outputs a scan signal according to the scan within the same plane of the terahertz waves 202 to a terahertz wave detecting portion 53. The scan signal is a signal that shows the coordinates within the same plane.

The terahertz wave detecting portion 53 detects the terahertz waves in the period while the terahertz wave generating portion 51 is radiating the terahertz waves 202. The terahertz wave detecting portion 53 outputs the detected signal to a spectrum calculating portion 54. At this time, the terahertz wave detecting portion 53 outputs a terahertz wave detection signal together with the scan signal received from the scanning portion 52 to the spectrum calculating portion 54.

The spectrum calculating portion 54 calculates a two-dimensional distribution of the spectrum based on the scan signal and the terahertz wave detection signal received from the terahertz wave detecting portion 53. An image producing portion 55 produces a two-dimensional image that shows the shape of the materials, based on the two-dimensional distribution of the spectrum calculated by the spectrum calculating portion 54 (second measurement spectrum two-dimensional distribution). The imaging portion 41 outputs the image data of the two-dimensional image produced by the image producing portion 55 to the image collating portion 42.

The description shall return to FIG. 9.

The image collating portion 42, upon receiving the image data from the imaging portion 41, performs collation with the image data in the image database 43. The image database 41 stores image data of collation images for collation with the two-dimensional image produced by the imaging. A collation image is for example an image that has the characteristics of an article that pertains to a hazardous material.

The image collating portion 42 outputs the collation result of the image data received from the imaging portion 41 and the image data in the image database 43 to an authenticating portion 6a. This collation result may for example be a value showing agreement or non-agreement with the collation image, or may be a graduated value showing similarity with the collation image.

The authenticating portion 6a, similarly to the first embodiment or the second embodiment, receives the combination or permutation of materials included in the terahertz authentication card 1 from the discriminating portion 4. Next, the authenticating portion 6a investigates whether that combination or permutation is stored in the authentication database 5. As a result, if the combination or permutation received from the discriminating portion 4 is stored in the authentication database 5, the following processing is performed. That is, the authenticating portion 6a judges whether the collation result received from the image collating portion 42 is abnormal or not abnormal in accordance with predetermined judgment conditions.

For example, in the case of the collation image being an image corresponding to a hazardous material, when the image of the imaging result and the collation image agree or are similar, there is judged to be an abnormality. In this case, if the collation result is a value that expresses the agreement or non-agreement with the collation image, it performs judgment as follows. When the collation result shows agreement with the collation image, the authenticating portion 6a judges there to be an abnormality. When the collation result shows non-agreement with the collation image, the authenticating portion 6a judges there to be no abnormality. Alternatively, in the case of the collation result being a graduated value expressing the similarity with the collation image, it performs a judgment as follows. When the collation result shows a similarity with the collation image of a certain value or greater, the authenticating portion 6a judges there to be an abnormality. When the collation result shows a similarity with the collation image of less than a certain value, the authenticating portion 6a judges there to be no abnormality.

The authenticating portion 6a outputs the authentication signal 202 to the controlled device 100 in the case of the collation result received from the image collating portion 42 showing no abnormality. The controlled device 100, upon receiving the authentication signal 202, starts a predetermined operation.

For example, the controlled device 100 may be the opening/closing device of the entrance gate of an airport. In this case, the image corresponding to a hazardous material is prepared as a collation image. In addition to the personal authentication by the terahertz authentication card 1, the presence of carrying of a hazardous material is distinguished based on the collation result between the image of the imaging result and this collation image. Thereby, only when personal authentication by the terahertz authentication card 1 is successful and there is no carrying of a hazardous material (there is no abnormality in the collation result of the image of the imaging result and the collation image), it is possible to perform control so as to open the entrance gate of the airport. As a result, the security check performance of an airport is markedly improves.

(Fourth Embodiment)

Figure 11:
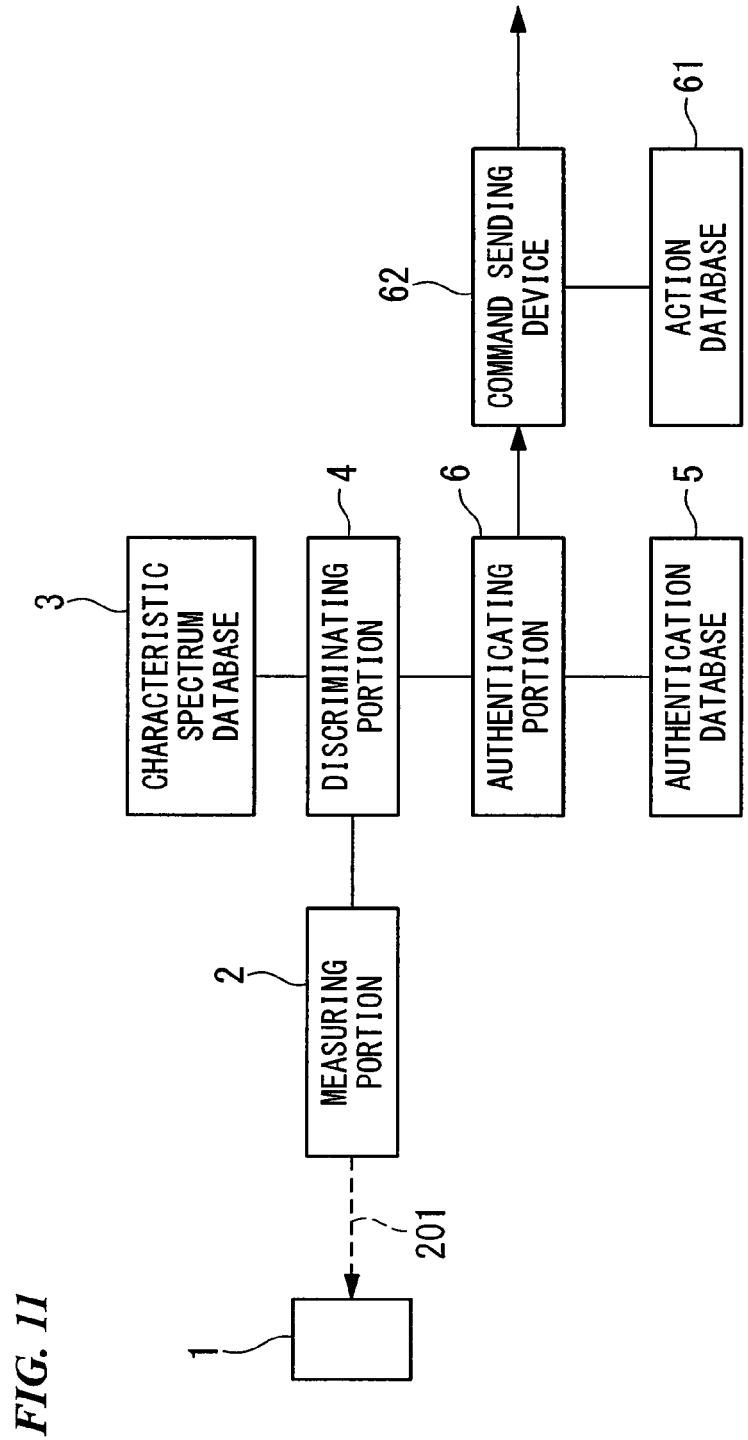
FIG. 11 is a block diagram showing a constitution of an authentication system according to the fourth embodiment of the present invention.

FIG. 11 is a block diagram showing the constitution of an authentication system according to a fourth embodiment of the present invention.

In FIG. 11, the same reference symbols are applied to the portions corresponding to each portion of FIG. 1. In the fourth embodiment, an action database 61 and a command sending device 62 are provided.

The action database 61 stores action information that shows what kind of operation the controlled device performs according to the authentication signal of the authenticating portion 6. The authentication signal referred to here is the user ID of the person who is successfully authenticated. The action database 6 stores action information for every user ID.

The command sending device 62 receives the authentication signal (user ID of the person who is successfully authenticated) from the authenticating portion 6. The command sending device 62 searches the action database 61 based on this user ID, and acquires the action information of the search result from the action database 61. The command sending device 62 sends the command that corresponds to the acquired action information (the application action) to the relevant controlled device (not illustrated in FIG. 11). The controlled device performs an operation in accordance with the received command.

The action information that is stored in the action database 61 specifies the operation content for every user ID. For example, the following is included in the case of controlling the door at the entrance to a store, and the entrance gate of an event site. The lock of the door or the gate is released to a certain user ID. For a different user ID, in addition to release the lock of the door or the gate, a voice message (for example, "Welcome, Mr. (user's name)") is played. For a different user ID, in addition to release the lock of the door or the gate, customer data of the user are displayed on a terminal in the store. Another example includes delivering information corresponding to the user ID (for example, digital signage). Besides these, application to a wide range of fields such as security fields and marketing fields is possible.

It is possible to combine the fourth embodiment with the first through third embodiments.

The embodiments of the present invention have been described in detail above with reference to the drawings, but the specific constitutions are not limited to the embodiments, and various design modifications are included within a range that does not depart from the gist of the present invention.

For example, in the embodiments described above, a card type (terahertz authentication card 1) has been given as an example of a portable medium for authentication, but the portable medium for authentication according to the present invention is not limited to a card type provided it is a portable shape.

Industrial Applicability

The present invention can be applied to various fields. Examples of applicable fields are given below.

(1) Application to a Security Gate of an Airport

In a conventional security gate in an airport, a person checks passengers' tickets. Furthermore, in addition to detecting metal that a passenger carries with a metal detector, a passenger's baggage is inspected by X-ray photography. Thereby, safety is ensured. By applying the present invention, it is possible to perform a check for the possession of hazardous materials and a check of baggage simultaneously with confirmation of a boarding pass (terahertz authentication card) just by the passenger passing through a radiation area of the terahertz wave while holding personal luggage.

(2) Application to a Security Check at an Office Such as a School or Company

In authentication by a conventional IC card, a student or clerical worker must hold up the IC card to an IC card reader. By applying the present invention, in the state of the student or clerical worker simply carrying a terahertz authentication card (for example, in the state of being in a pocket or briefcase), if the student or clerical worker passes through a radiation area of the terahertz wave, it is possible to perform authentication. Thereby, it is possible to prevent entry accompanied by others who are not authenticated, and forgetting to hold up the card.

(3) Application to the Marketing Field

In a store's customer reception system, by authenticating a card of a person who comes to the store in accordance with the present invention, it is possible to individually greet customers.

In a digital signage system, when a terahertz authentication card holder approaches the digital signage area, it is possible to refer to a database and display an optimal advertisement (matching advertising becomes possible) in accordance with the present invention.

(4) Application to the Welfare Field

In accordance with the present invention, by reading information from a terahertz authentication card that is on the body of a physically handicapped person, it is possible to open doors without performing an action such as pressing a button, and it is possible to display information for providing optical services to disabled people.

The invention claimed is:

1. An authentication system comprising:
   a measuring portion that radiates terahertz waves to a portable medium for authentication including materials having a characteristic oscillation frequency in a terahertz frequency band while scanning in a two-dimensional manner, measures a two-dimensional distribution of a spectrum, and outputs a first measurement spectrum two-dimensional distribution that is a measurement result;
   a characteristic spectrum database which stores a characteristic spectrum of the materials;
   a discriminating portion that discriminates the materials that are included in the portable medium for authentication based on the first measurement spectrum two-dimensional distribution and the characteristic spectrum and acquires a discrimination result, the discriminating portion judging a permutation in a two-dimensional spatial relation of the materials determined by the discrimination result;
   an authentication database which stores at least a plurality of permutations of materials that are included in the portable medium for authentication, the permutations differing from one another, a combination of materials which constitute one of the permutations being the same as a combination of materials which constitute each one of the other permutations; and
   an authenticating portion that determines whether the permutation judged by the discriminating portion is the same as any one of the permutations stored in the authentication database, the authenticating portion outputting an authentication signal upon determining that the permutation judged by the discriminating portion is the same as any one of the permutations stored in the authentication database.

2. The authentication system according to claim 1, further comprising a controlled device that operates in accordance with the authentication signal.

3. The authentication system according to claim 1, further comprising:
   an imaging portion that radiates terahertz waves to a holder of the portable medium for authentication while scanning in a two-dimensional manner, measures a two-dimensional distribution of a spectrum and acquires a second measurement spectrum two-dimensional distribution that is a measurement result, and produces a two-dimensional image that shows a shape of a material that the holder is carrying based on the second measurement spectrum two-dimensional distribution;
   an image database that stores a collation image for collation with the two-dimensional image that is produced by the imaging portion; and
   an image collating portion that collates the two-dimensional image that is produced by the imaging portion with the collation image in the image database, and outputs a collation result,
   wherein the authenticating portion performs authentication on the holder based on the collation result.

4. The authentication system according to claim 1, further comprising:
   an action database that stores action information that shows what kind of operation a controlled device that operates according to a command performs; and
   a command sending portion that searches for application action information according to the authorization signal from the action database, and transmits a command corresponding to the application action information to the controlled device.

* * * * *